US00PP08427P

United States Patent [19]

Jessel, Jr.

[11] Patent Number: Plant 8,427

[45] Date of Patent: Oct. 19, 1993

[54] CARNATION PLANT NAMED CFPC PRISTINE

[75] Inventor: Walter H. Jessel, Jr., Salinas, Calif.

[73] Assignee: California Florida Plant Co., L.P., Salinas, Calif.

[21] Appl. No.: 950,307

[22] Filed: Sep. 24, 1992

[51] Int. Cl.[5] ..... A01H 5/00

[52] U.S. Cl. ..... Plt./70.3

[58] Field of Search ..... Plt./70.3

*Primary Examiner*—Howard J. Locker

*Attorney, Agent, or Firm*—Christie, Parker & Hale

[57] ABSTRACT

A new carnation of pure white coloration.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation. The varietal denomination of this new carnation is 'CFPC Pristine'.

Among the novel combination of characteristics possessed by the new variety which distinguishes it are flowers of pure white coloring which does not reduce its bud count during winter.

Asexual reproduction by propagation by side shoot cuttings of the new variety as performed in Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Pristine'.

BRIEF DESCRIPTION OF THE ILLUSTRATION

The accompanying illustration shows typical specimens of the vegetative growth and flowers in different stages of development of the new variety depicted in color as nearly true as it is reasonably possible to make the same in a color illustration of this character.

DESCRIPTION OF THE NEW VARIETY

The following is a detailed description of my new variety, with color terminology in accordance with the Royal Horticultural Society Colour Chart (RHSCC). The terminology used in the color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont, Calif. The height of plant and flower and foliage size are established as an average using standard commercial cultural practices.

Name: 'CFPC Pristine'.

Classification:

*Botanical.*—*Dianthus caryophyllus.*

*Commercial.*—Carnation, spray type.

Parentage:

*Female parent.*—Unnamed seedling (No. 870914).

*Male parent.*—Unnamed seedling (No. 870642).

Plant:

*Height.*—About 31 inches.

*Growing habit.*—Herbaceous, semi-upright.

*Blooming habit.*—Terminal as a spray.

*Blooming season.*—Year round.

*Rooting time.*—About 14-15 days.

*Mutation prone.*—Does not appear to be.

*Disease resistance.*—Unknown.

*Temperature tolerance.*—Typical for carnation.

*Breaking action.*—Very good.

Foliage:

*Color.*—Upper side: Near 139A. Lower side: Near 143A.

*Size.*—About 4 inches long at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About 1½ inches.

*Diameter.*—About ½-inch.

Calyx:

*Number of sepals.*—About 5.

*Length.*—About 1-inch.

*Width.*—About ¼-inch.

Color.—Outside — near 143B. Inside — near 142D.

Bloom:

*Shape.*—Round.

*Size.*—Diameter average: About 2 inches. Depth average: About 1½ inches.

*Borne.*—Terminal as a spray.

*Color.*—General tonality: Pure white. Upper side: Whiter than 155D. Lower side: Near 155D. Center: Near 155D. Outer petals: Whiter than 155D.

*Keeping quality.*—Good.

*Fragrance.*—Slight.

Petals:

*Number.*—About 41.

*Outer petals.*—Length: About 1½ inches. Width: About 1-inch.

*Central petals.*—Length: About 1-inch. Width: About ½-inch.

*Texture.*—Smooth.

*Form.*—Fan shaped.

*Appearance.*—Shiny.

Reproductive organs:

*Stamens.*—Number: About 11. Arrangement: Around the ovary.

*Anthers.*—Length: About 1/9-inch. Color: Near 160D.

*Filaments.*—Length: About 1¼ inches. Color: Near 155D.

*Pistil.*—Number: About 3. Color: Near 155A.

*Stigma.*—Number: About 3. Color: Near 155A.

*Ovary.*—Shape: Conical. Color: Base — green. Body — green. Apex — tan.

*Fertility.*—Male — poor. Female — poor.

I claim:

1. A new and distinct variety of carnation plant, substantially as shown and described.

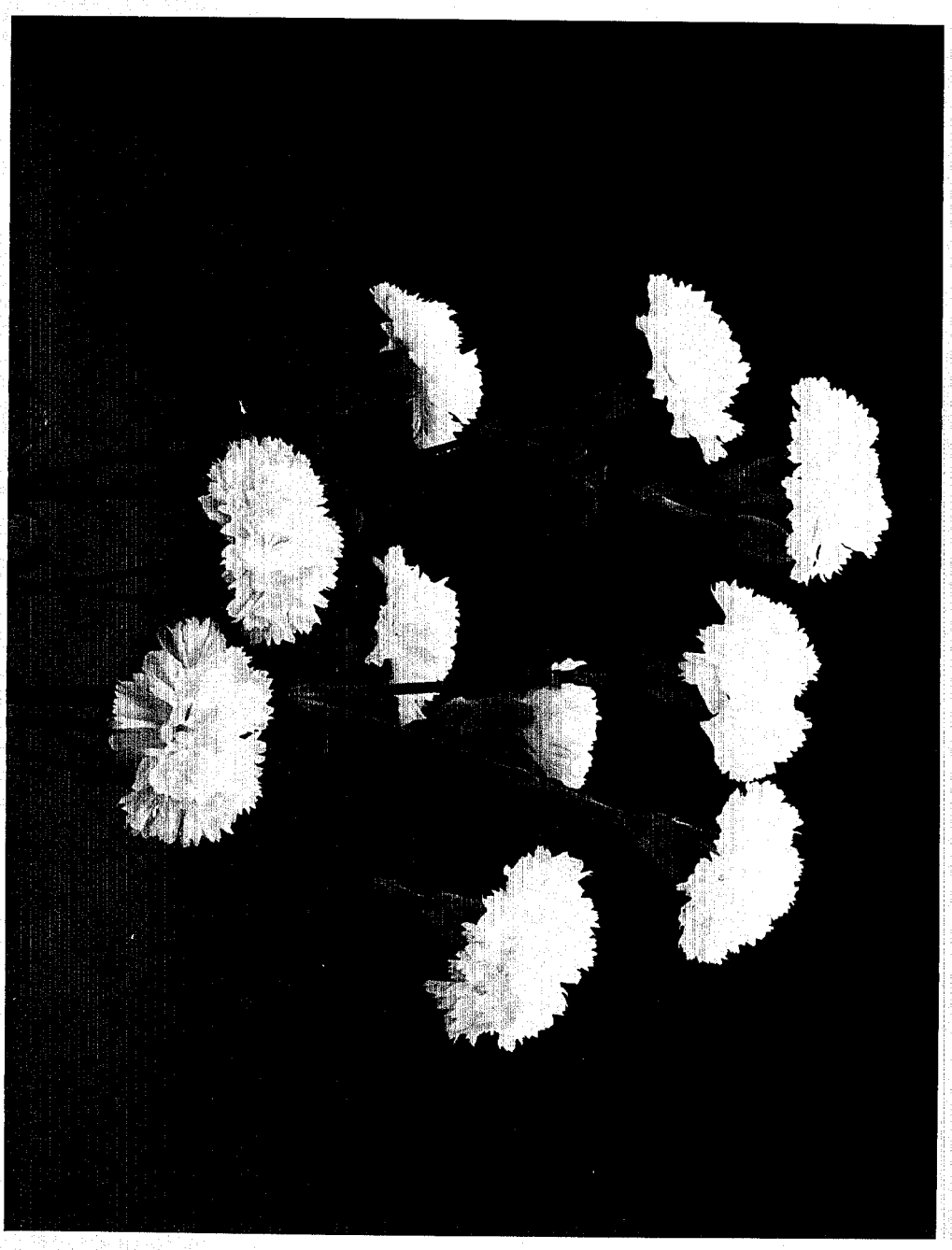

* * * * *